United States Patent
Gallup et al.

[11] Patent Number: 6,132,686
[45] Date of Patent: Oct. 17, 2000

[54] PRESSURIZED REACTION BLOCK

[75] Inventors: David A. Gallup, Schaumburg, Ill.; James R. Harness, Hastings, Mich.; Rudy H. Haidle, Evanston, Ill.; Andrew J. Grzybowski, Spring Grove, Ill.; Larry W. Markus, Mundelein, Ill.

[73] Assignee: Mettler-Toledo Bohdan, Inc., Vernon Hills, Ill.

[21] Appl. No.: 09/322,566

[22] Filed: May 28, 1999

[51] Int. Cl.$^7$ ...................................................... B01J 19/00
[52] U.S. Cl. ........................... 422/130; 422/99; 422/100; 422/129; 422/131
[58] Field of Search ............................. 422/99, 100, 101, 422/103, 129, 130, 131, 138, 135

[56] References Cited

U.S. PATENT DOCUMENTS

| | | |
|---|---|---|
| 4,517,338 | 5/1985 | Urdea et al. . |
| 4,598,049 | 7/1986 | Zelinka et al. . |
| 4,671,941 | 6/1987 | Niina et al. . |
| 4,746,490 | 5/1988 | Saneii . |
| 4,748,002 | 5/1988 | Neimark et al. . |
| 5,143,854 | 9/1992 | Pirrung et al. . |
| 5,252,296 | 10/1993 | Zuckermann et al. . |
| 5,380,495 | 1/1995 | Chang et al. . |
| 5,395,594 | 3/1995 | Nokihara et al. . |
| 5,503,805 | 4/1996 | Sugarman et al. . |
| 5,716,584 | 2/1998 | Baker et al. . |
| 5,762,881 | 6/1998 | Harness et al. . |
| 5,866,342 | 2/1999 | Antonenko et al. ...................... 435/7.1 |
| 5,888,830 | 3/1999 | Mohan et al. ........................... 436/174 |
| B1 5,324,483 | 9/1996 | Cody et al. . |

FOREIGN PATENT DOCUMENTS

| | | | |
|---|---|---|---|
| 0529504 A2 | 3/1993 | European Pat. Off. ......... | B01J 19/00 |
| WO97/09353 | 3/1997 | WIPO . | |

*Primary Examiner*—T. Tung
*Assistant Examiner*—Dwayne K. Handy
*Attorney, Agent, or Firm*—McEachran, Jambor, Keating, Bock & Kurtz

[57] ABSTRACT

A reaction block assembly of reaction vessels for conducting chemical reactions under pressure. The assembly includes a heat conductive reactive block having reaction vessel receiving openings formed in the block. A heat exchanger is mounted in heat transfer engagement with some of the exterior walls of the reaction block. The heat exchangers can operate in different modes, to provide a heat differential across the reaction block. A reaction vessel is positioned in each reaction vessel receiving opening in the block. A cap is attached to each reaction vessel and a cannula opening is formed in each cap. A cannula passage is connected at one end to a cannula opening in each cap and it has a septum at the other end. A valve controls each cannula passage. An operating mechanism is provided for opening and closing each cannula passage controlling valve. The reaction block assembly may be used to determine when the reaction of a solution in a reaction vessel is completed. This is accomplished by using a calibration curve comparing the frequency of rotation of the stirring bar with the viscosity of the reaction solution in which the frequency is inversely proportional to the viscosity. The time interval at which the stir bar decouples from rotation with the driving magnet is determined. This time interval of decoupling is compared with the calibration table to determine the viscosity of the solution at the time the reaction was completed which takes place at the time the stir bar was decoupled.

10 Claims, 9 Drawing Sheets

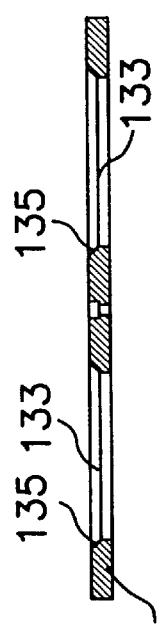
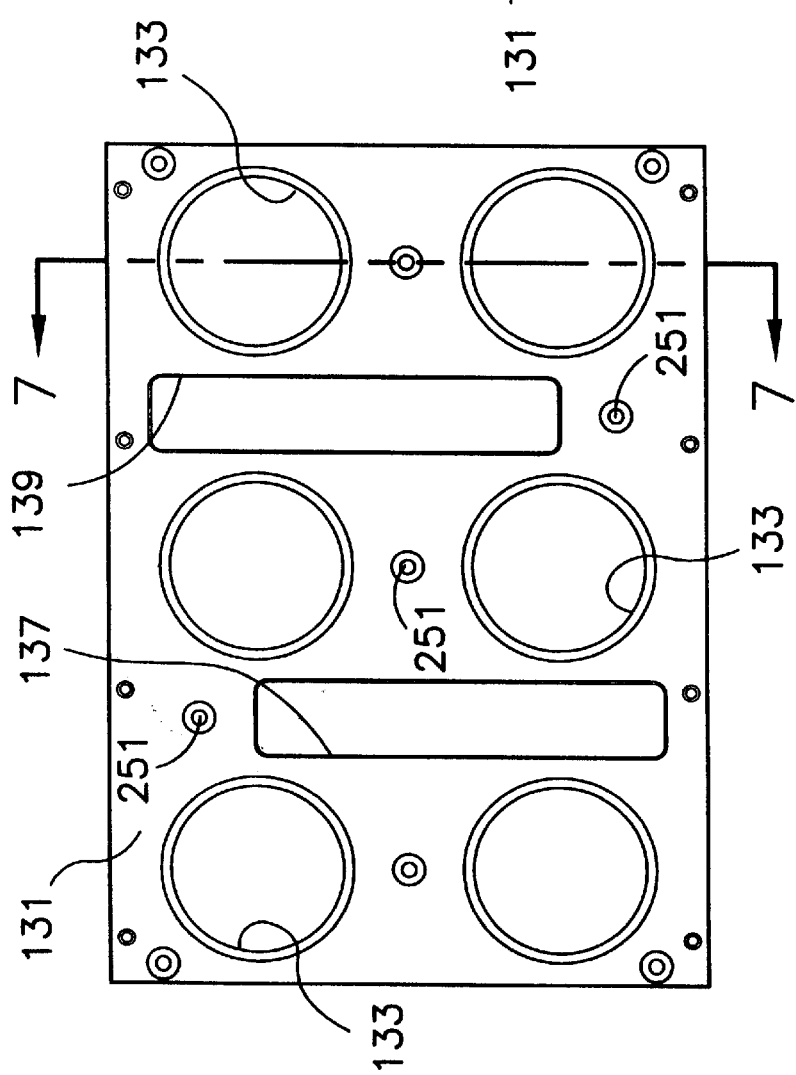

PRESSURIZED REACTION BLOCK

BACKGROUND AND SUMMARY OF THE INVENTION

This invention is directed to a reaction block for pressurized combinatorial chemistry reactions which can be incorporated into an automatic work station for computer controlled performance of automated synthesis support for the reaction vessels supported in the reaction block.

The reaction block of this invention accommodates modular arrays of pressurizable reaction vessels with each modular array being transportable in its own carrier for reception into and removal from the reaction block. For ease of handling, two carriers are provided to handle the reaction vessels which are accommodated by a single reaction block.

The reaction block of this invention is intended for fully automated operation with pressurized reaction sequences controlled and monitored by a computer and software with the control extending to all of its operating parameters relating to temperatures, pressures, status of operating valves, whether open or closed, sequence of heating, addition of reaction components, stirring of the reacting chemicals to desired viscosities, monitoring of reaction and pressurizing gases and detection of flammable gases, both those generated by the chemical reactions and those introduced into the reactions.

A feature of this invention is a reaction block having reaction vessels capable of reacting chemicals at pressures above 30 psi.

Another feature of this invention is a reaction block which is capable of reacting chemical solutions at high pressures while also having the capability of permitting the addition of reaction components to the reaction vessels at lower pressures and then increasing the pressures in the reaction vessels to much higher pressures to complete the reactions.

Another feature of this invention is a reaction block having pressurized reaction vessels which can be supplied with reaction components both while under ambient pressures and low pressures through the use of cannulas.

Another feature of this invention is a reaction block having the ability to handle complex chemical reactions of the type which require that liquid reactants be introduced into the reaction vessels while the chemicals being reacted are still under relatively low pressures.

Another feature of this invention is a reaction block having pressurized reaction vessels equipped with removable glass vial liners.

Another feature of this invention is a carrier for a modular array of reaction vessels which carrier also supports cannula tubes, septums and the valves controlling the cannula tubes which provide access to the reaction vessels of the modular array.

Another feature of this invention is a simplified method and apparatus for determining when a chemical compound being reacted in a reaction vessel is fully reacted.

Another feature of this invention is a simplified method and apparatus for determining the viscosity reached by a chemical compound being reacted at the end of its reaction which method and apparatus utilizes a magnetic detector such as a single Hall Effect switch, a magnetostrictive detector or a loop of wire.

Other features and advantages of the invention will be found in this following specification, claims and drawings.

BRIEF DESCRIPTION OF THE DRAWINGS

The invention is illustrated more or less diagrammatically in the following drawings wherein:

FIG. 6 is a top plan view of a carrier capture plate of the type shown as part of the carrier in FIG. 5 of the drawings;

FIG. 7 is a cross sectional view taken along line 7—7 of FIG. 6;

DESCRIPTION OF THE PREFERRED EMBODIMENT

Figure 1:
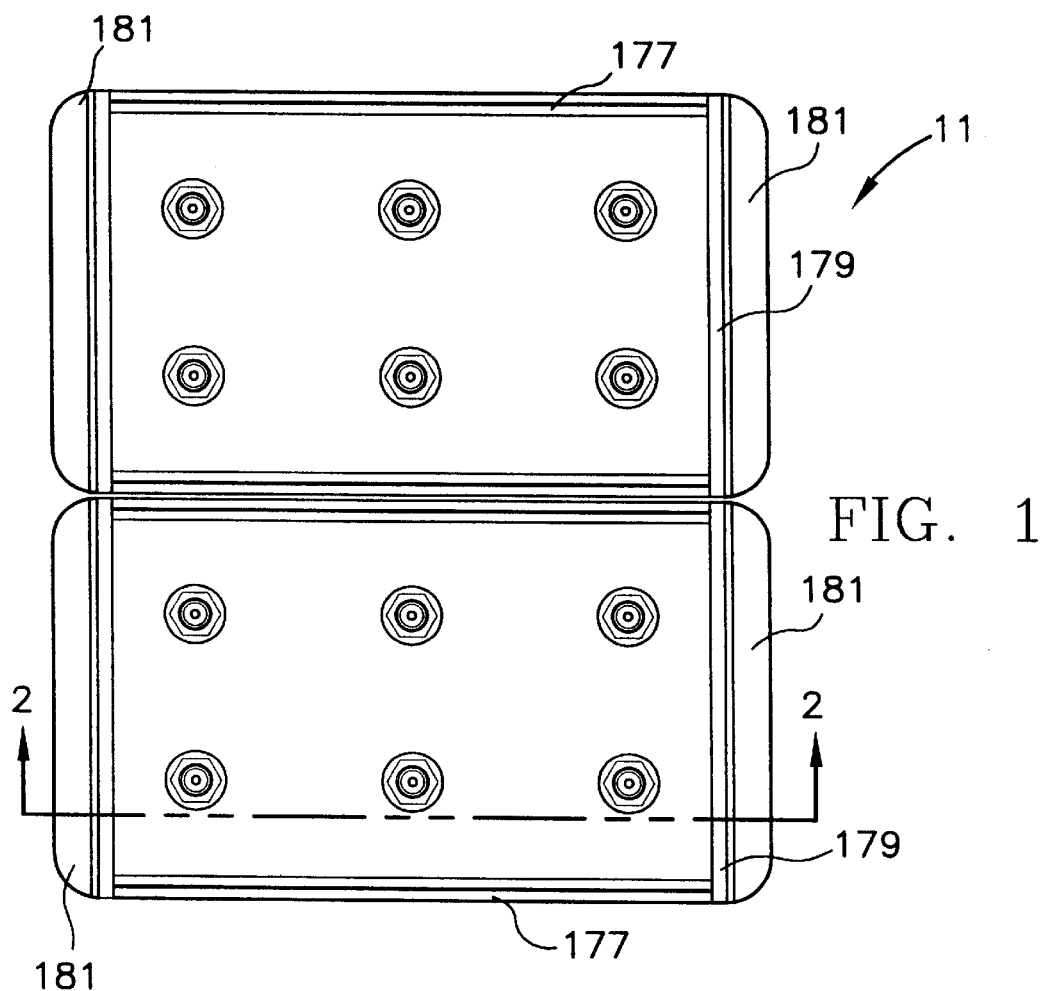
FIG. 1 is a top plan view of the reaction block assembly of this invention with the carriers for the modular arrays of reaction vessels positioned thereon and with some parts omitted for clarity of illustration.

The drawings, FIGS. 1–13, show the invention incorporated in a reaction block assembly 11, which, in this embodiment of the invention, is adapted to hold and react twelve reaction vessels 13 at a time. The reaction vessels are arranged in modular arrays of six reaction vessels each. A carrier 15 is provided for each modular array of six reaction vessels. The carriers also support a cannula access and control system 17 for the reaction vessels. A pressurized gas system 19 shown in FIG. 13 is provided to supply air, inert gases and reactant gases at low and high pressures to the reaction vessels. The gas system also supplies venting, pressure relief and vacuum as indicated by the labeling shown in FIG. 13. A magnetic stirring system 21 is provided beneath the reaction block assembly 11 for magnetic stirring of the contents of the reaction vessels while the contents are being reacted.

Figure 2:
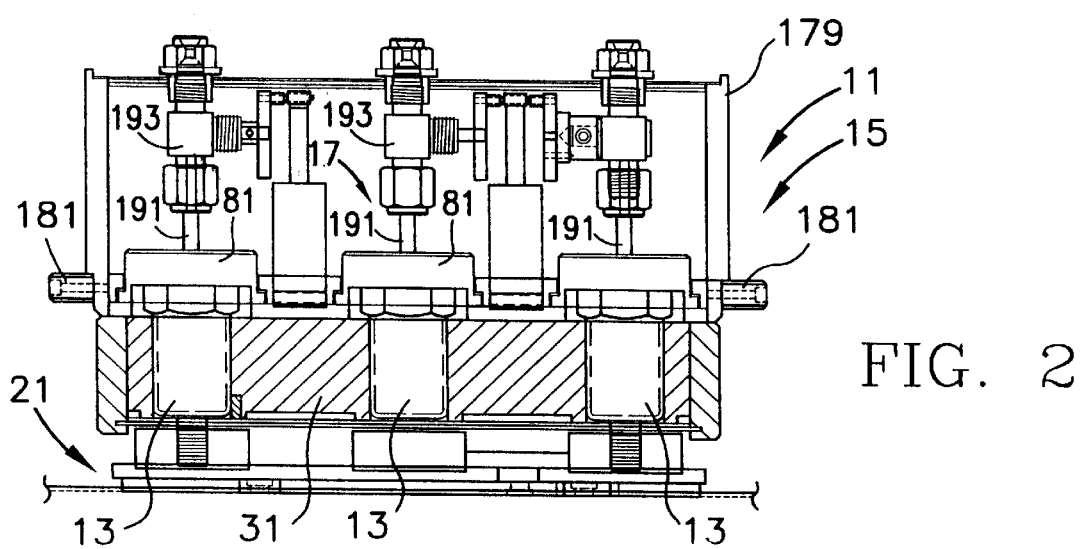
FIG. 2 is a cross sectional view of the reaction block assembly taken along line 2—2 of FIG. 1 with some parts removed for clarity of illustration.
Figure 3:
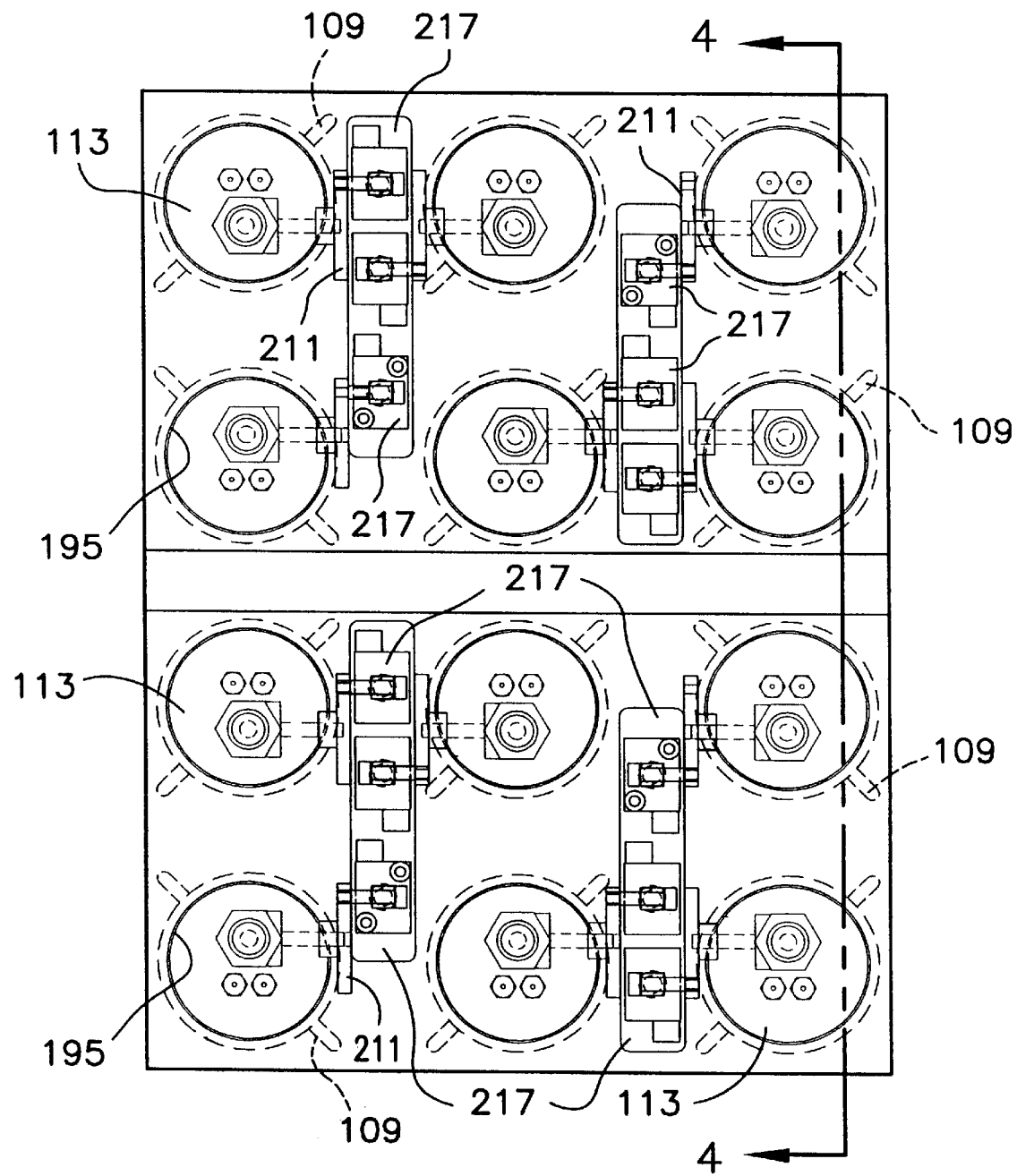
FIG. 3 is a top plan view of the reaction block assembly of this invention with portions of the carrier covers broken away and with some hidden parts shown in dashed lines.
Figure 4:
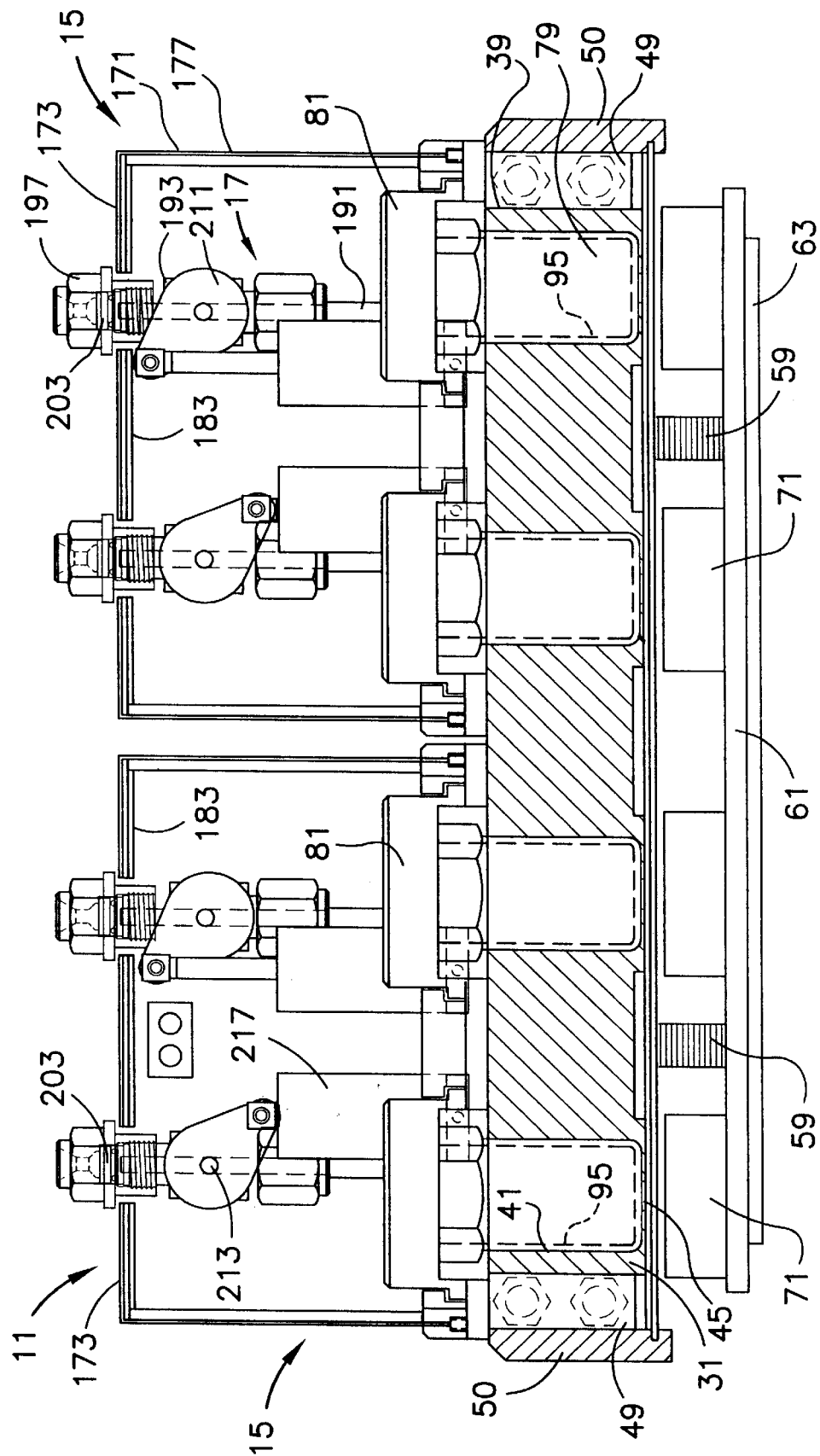
FIG. 4 is a cross sectional view of the reaction block assembly taken along line 4—4 of FIG. 3 with some hidden parts shown in dashed lines.
Figure 5:
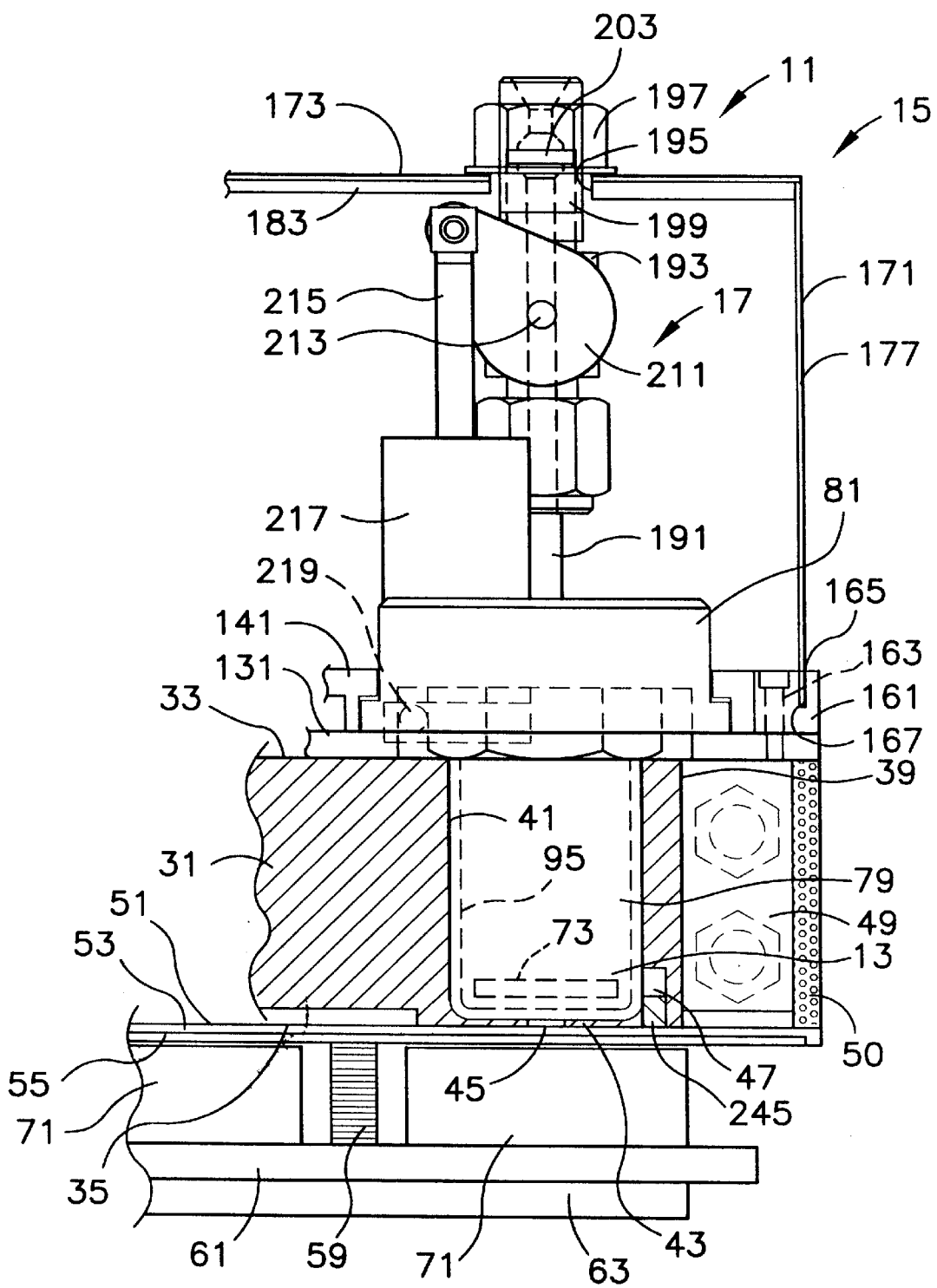
FIG. 5 is an enlarged partial view of a portion of the reaction block showing a single reaction vessel with some parts broken away, some shown in cross section and some hidden parts shown by dashed lines.

An aluminum reaction block 31, which is rectangular in horizontal cross section, is shown most clearly in detail in FIGS. 2, 4 and 5 of the drawings. The reaction block includes a top surface 33, a bottom surface 35, end walls 37 and side walls 39. Reaction block containing cavities 41 are formed in the top surface 33 and extend to the bottom surface 35 of the reaction block terminating in a thin wall 43 at the base of each cavity 41.

In this embodiment of the invention, there is an array of twelve cavities 41 formed in the reaction block 31 and arranged in a pattern of 3 cavities×4 cavities. A small opening 45 is formed in the thin wall 43 at the bottom of each cavity 41 to improve air flow through the cavity. A socket 47, shown in FIG. 5, extends upwardly from the bottom surface, 35 of the aluminum reaction block 31 to provide a housing for a detector such as a Hall effect switch to be described hereinafter. Although this embodiment of the invention shows the reaction vessel receptacles as cavities 41, it should also be understood and appreciated that although passages through the block may be used for this purpose, it has been found that providing a cavity with a thin bottom wall 43 provides improved heat transfer through the reaction block to the bottoms of each reaction vessel 13. The heat is provided by heat transfer elements 49 which are attached to the side walls 39 of the block. These heat transfer elements are conventionally supplied by hot water or steam but, of course, could also be powered by electricity depending on the operating parameters of the reaction block assembly. Cooling may be provided by chilled water or in any other conventional manner. The oppositely located heat exchangers 49 may be arranged so that one is supplying heat and the other supplying cooling so that a heat differential is obtained across the reaction vessels. An insulating panel 50 is installed on the outer surface of each heat transfer element 49.

The bottom surface 35 of the reaction block 31 rests on an insulation sheet 51 of a foam cell insulation of the type sold under the trademark ROHACELL. The insulation sheet 51 rests on a sheet 55 of epoxy glass of the type used for printed circuit boards. Posts 59 located between the reaction vessels 13 engage and support the lower sheet 55 of epoxy glass. The posts are supported on an aluminum base 61 which is supported on a locator base 63. A magnetic stirrer motor 71 is provided under each reaction vessel 13. A magnetic stir bar 73 which is rotated by the magnetic stirrer motor is provided in each reaction vessel to mix the reacting chemical solution until it reached the desired viscosity.

Figure 12:
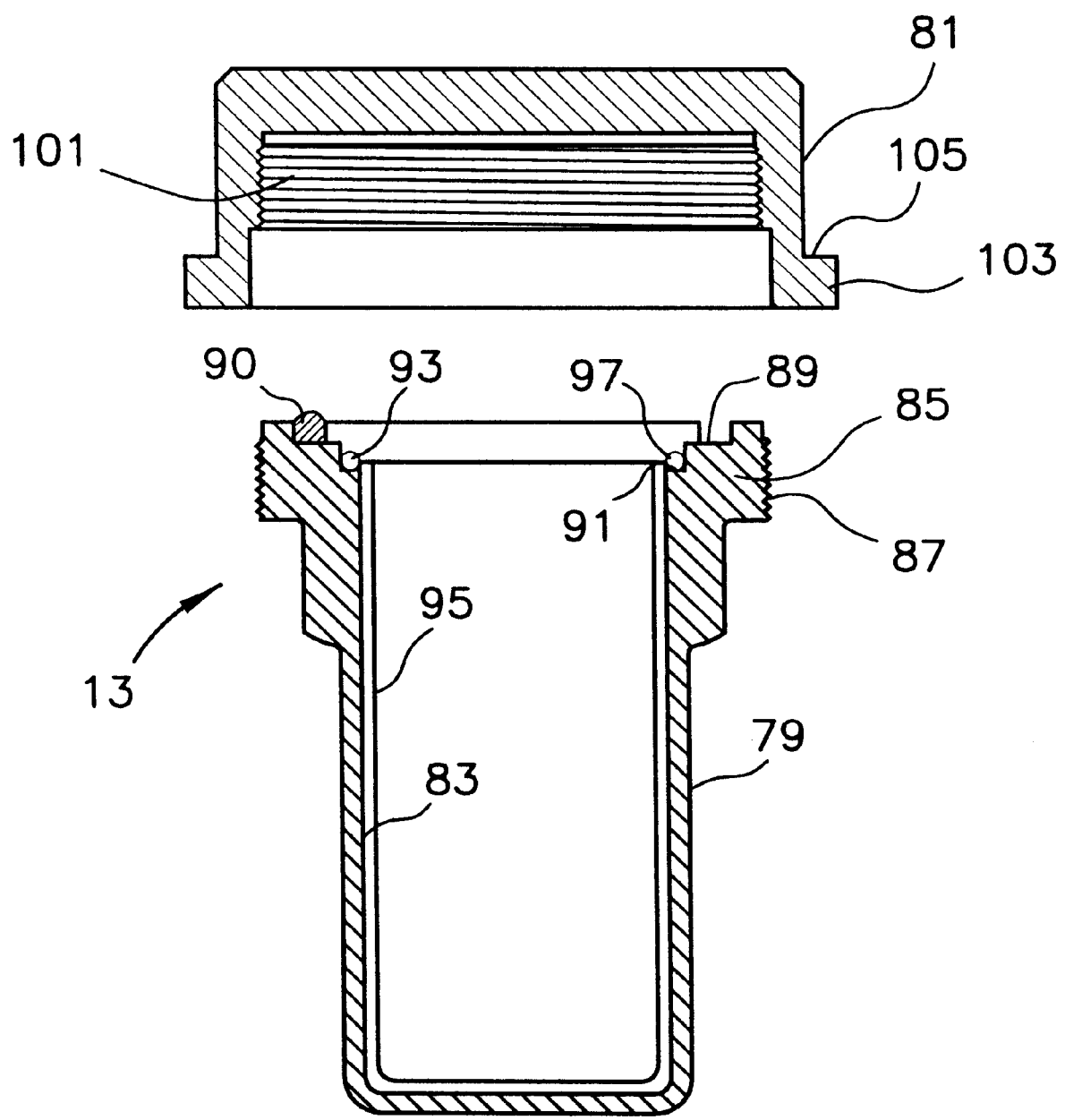
FIG. 12 is an exploded view of a reaction vessel and its cap with some elements of the cap omitted for clarity of illustration.
Figure 13:
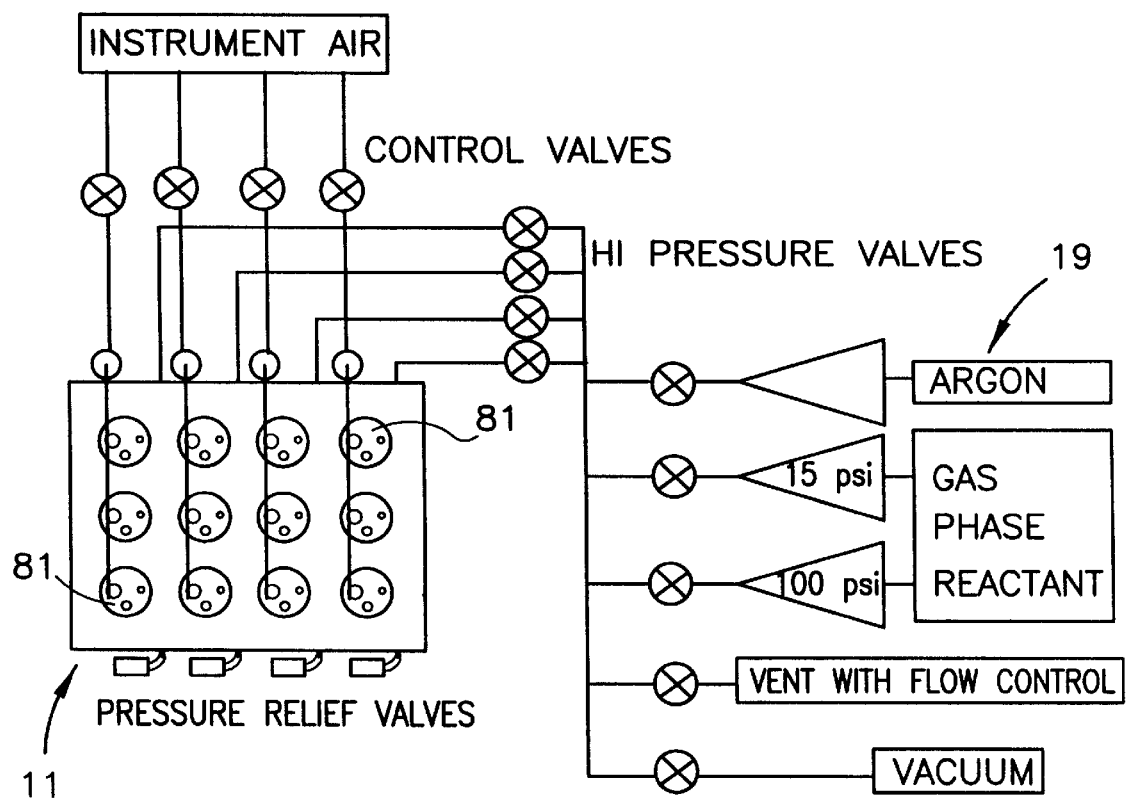
FIG. 13 is a schematic of the gas and air supplies for the reaction vessels.

The reaction vessels 13 are shown generally in FIGS. 2 and 4 and in detail in FIGS. 5, 9, 10 and 12 of the drawings. The reaction vessels are made of a non-magnetic stainless steel and include a cup 79 and a cap 81. The cup has a cavity 83 and a flange 85 which, for orientation purposes, will be referred to as located at the upper end of the cup. External threads 87 are formed on the flange 85. An O-ring groove 89 is formed in the top surface of the flange as shown in FIG. 12 of the drawings. This groove receives an O-ring 90 which engages the cap for sealing purposes as can be best seen in FIG. 12 of the drawings. A shoulder 91 is formed in the cavity 83 near the upper end thereof and a shallow notch 93 is formed in this shoulder. A glass vial liner 95 seats in the cavity 83 of the cup 79 and extends above the shoulder 91. The notch 93 provides a pathway between the cavity 83 of the cup 79 and the interior of the glass vial to equalize pressure inside and outside of the vial. An O-ring 97 seats on the shoulder 91 between the glass vial liner 95 and the wall of the cavity 83. The O-ring engages the vial and the shoulder 91 to prevent rotation of the vial.

Figure 10:
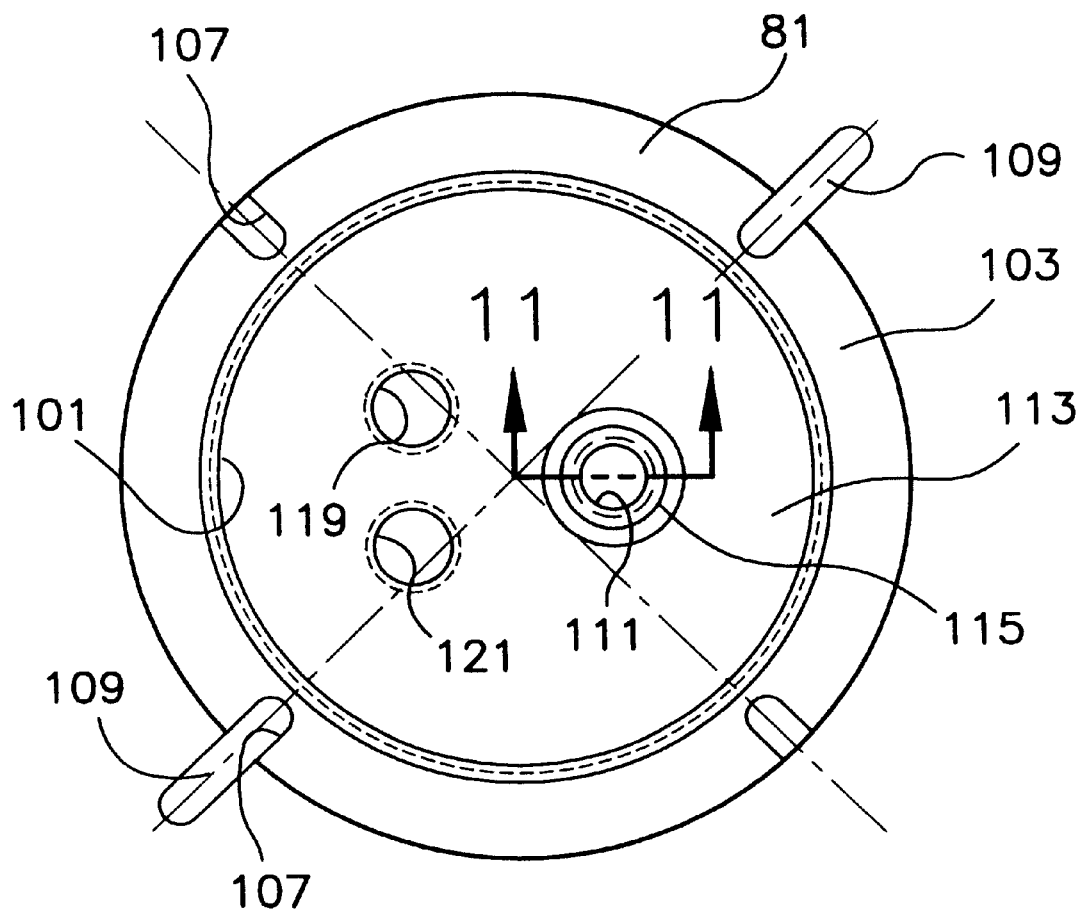
FIG. 10 is an enlarged, bottom plan view of a reaction vessel cap.
Figure 11:
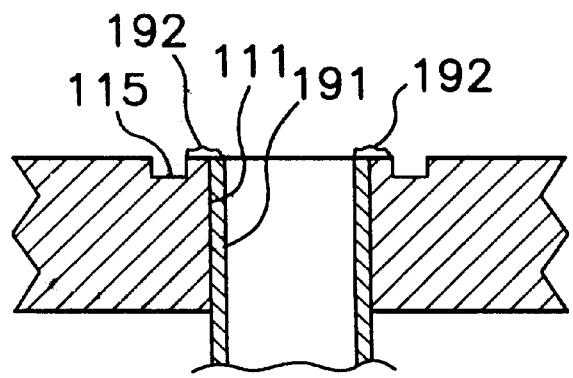
FIG. 11 is an enlarged view taken along line 11—11 of FIG. 10.

The reaction vessel cap 81 shown in details in FIGS. 10, 11 and 12 of the drawing has internal threads 101 which engage the external threads 87 on the flange of the reaction vessel 13 to connect the cap to the reaction vessel. The cap includes a flange 103 with a shoulder 105 formed on the top of the flange. Notches 107 are formed in the bottom of the flange with each notch being located 90 degrees apart around the perimeter of the flange. The notches are intended to receive rods 109 with two rods installed in each cap. The rods are positioned in notches which are 90 degrees apart for alignment and orientation of the cap to be explained hereinafter.

A cannula passage 111 is formed in the top wall 113 of the cap. A weld groove 115 surrounds the cannula passage 111. A threaded gas passage 119 and a threaded temperature probe passage 121 are formed in the cap. The cannula passage 111 is located in one quadrant of the cap as defined by the notches 107. The gas and temperature passages 119 and 121 are located in a diagonally oppositely located quadrant also defined by the notches 107 for orientation of the cap 81 relative to the cannula passage, the temperature probe passage and the gas supply conduit as will be hereinafter described.

Two carriers 15 are provided, one for each modular array of pressure vessels 13. FIG. 5 shows the location of capture plate 131 forming a part of a carrier and its details are shown in FIGS. 6 and 7 of the drawings. Each capture plate 131 has six reaction vessel receiving passages 133. Each passage is formed with a funnel shaped throat 135 for receiving a reaction vessel 13. Rectangular passages 137 and 139 located between the reaction vessel receiving passages are formed to extend through the capture plate. These rectangular passages are staggered in relation to the side walls of the capture plate in order to properly receiving air cylinders which will be hereinafter described.

Figure 9:
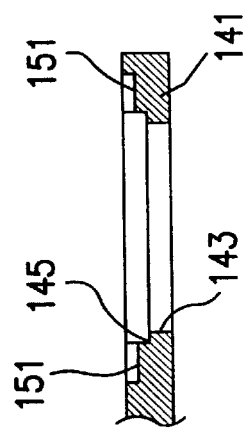
FIG. 9 is a cross sectional view taken along line 9—9 of FIG. 8.
Figure 8:
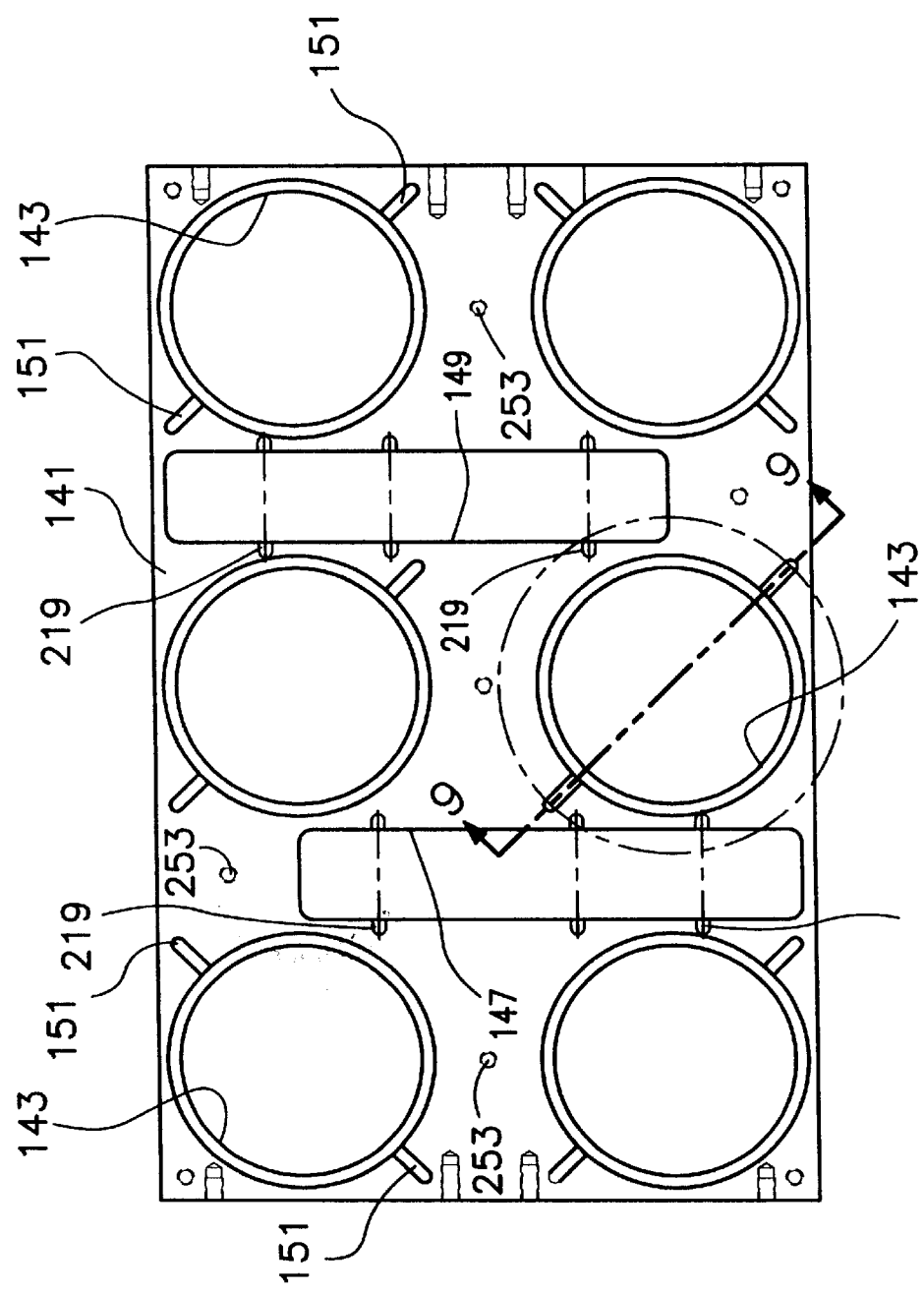
FIG. 8 is a bottom plan view of the upper plate of a carrier which plate is shown assembled on the carrier in FIG. 5 of the drawings.

Each carrier 15 also includes an upper plate 141 shown assembled in a carrier in FIG. 5 and in detail in FIGS. 8 and 9 of the drawings. Six passages 143, each adapted to receive the upper portion of a reaction vessel cap 81, extend through the upper plate. Each passage also is formed with an enlarged cutaway 145 for the reaction vessel cap flange 105. Rectangular passages 147 and 149 are formed to extend through the upper plate. These passages are similar in size and location to the rectangular passages 137 and 139 in the capture plate and are aligned with passages 137 and 139 when the upper plate and the capture plate are assembled in a carrier. A pair of aligned, radially extending slots 151 are formed in the lower surface 153 of the upper plate to receive the rods 109 attached to the flange 103 of a reaction block cap 81 for alignment of the cap and also its cannula passage 111, air supply conduit 119, and temperature probe passage 121 as shown most clearly in FIGS. 3 and 8 of the drawings. The capture plate 131 is fastened to the upper plate by threaded fasteners, not shown, which extend through threaded holes in the plates. The capture plate 131 and the upper plate 141 of the carrier restrain the caps 81 of the reaction vessels 13 while permitting the cups 79 of the reaction vessels to be removed from the caps when the carrier 15 is removed from the reaction block 11.

Other aspects of a carrier 15 are shown in detail in FIG. 5 and generally in FIGS. 1, 2, 3 and 4 of the drawings. A rim 161 is attached to the capture plate 131 by fasteners 163. The rim 161 may be formed of a glass fiber silicon laminate sold under the trademark G-7. This rim has an upwardly opening slot 165 which receives the edges 167 of stainless steel side walls 169 of a module array cover 171. This cover is formed with a roof 173, but no end walls. The ends of the cover are closed by walls 179 formed of closed cell foam insulation such as is sold under the trademark ROHACELL, which walls are attached to the upper plate 141 of a carrier 15 at the opposite ends thereof. Lifting handles 181 are attached to the end walls 179. A printed circuit board 183 is supported on the top surfaces of walls 179 to be positioned immediately below the roof 173 of the cover 171.

The cannula access system 17 includes cannula tubes 191 each of which connects to the passage 111 in a reaction vessel cap 81 as is shown most clearly in FIGS. 1, 2, 3, 4 and 5 of the drawings. The cannula tube is welded to the cap 81 as shown in FIG. 11 with the weld 192 positioned between the end of the tube 191 and the weld groove 115 formed in the cap around the passage 111. Each cannula tube 191 is controlled by a control valve 193 which in this embodiment of the invention is a plug valve. The cannula tubes are accessible through passages 195 formed in the roof 173 of the carrier cover 171. Each passage is closed by a septum housing 197 which also functions as a fastener for the module array cover 171 and as a guide for insertion of the cannula into the cannula tube 191. The septum housings thread onto threaded fittings 199 at the upper ends of the cannula tubes. A septum 203 is located in each of the septum housings.

Each plug valve 193 is operated by a lever 211 which is attached to the valve by a shaft 213. The lever is rotated about the shaft 213 by means of a rod 215 which is driven by a double action air cylinder 217. The air cylinders are pivotally mounted on trunions 219 which are located in sockets 221 formed in the rectangular passages 147 and 149 of the upper plate. The air cylinders extend through the rectangular passages of the upper plate and partially into the rectangular passages 137 and 139 of the capture plate 131 as is best depicted in FIG. 5 of the drawings.

The use, operation and function of this invention are as follows:

The reaction block assembly 11 of this invention is used for chemical reactions such as hydrogenation, carbonization and polymerization under pressure. The chemicals to be reacted, generally in solid form, are placed in the glass vial liners 95 in the cups 79 of the reaction vessels 13. The caps 81 of the reaction vessels are positioned in a capture plate 131 of a modular carrier 15 with their aligning rods 109 seated in the notches 107 of the flanges 103 of the caps. The upper plate 141 of a modular carrier 15 is positioned on the capture plate 131. The aligning rods 109 of the caps seated in the slots 151 formed in the lower surface of the upper plate 141 of the carrier orient the cannula outlets 111, gas outlets 119 and temperature outlets 121 of the caps relative to their respective cannula tubes 191, temperature probe passages and gas supply conduits and plug valves 193. The upper plate is then connected to the capture plate by threaded fasteners (not shown) which extend through aligned openings 251 and 253 located respectively in the capture plate and the upper plate. The reaction vessel caps 81 are thus held between these plates. The cannula tubes, gas conduits and temperature probes are connected to the reaction caps. The reaction vessel cups 79 holding the chemicals to be reacted are threaded onto their caps 81.

The protective cover 171 is placed on the modular carrier 15 and cannula tube housings 197 are threaded onto the cannula tubes 191 to fasten the protective cover to the modular carrier. The modular carrier with its protective cover is positioned on the reaction block 31. The second modular carrier is also positioned on the reaction block locating reaction vessels in all of the reaction block vessel receiving cavities. The gas conduits and temperature probes are then connected to the reaction vessels.

A vacuum is applied to the reaction vessels through the gas conduit. Pressurized insert gas is introduced through a manifold and the gas conduit to the reaction vessels 13 to purge them. Solvents or liquid reactants maybe introduced to the reaction vessels through the cannulas. The septums 203 installed in the septum housings 197 are designed to withstand pressures of up to 15 psi, which is considered in this application as low pressure. While under such low pressure, reaction chemicals in liquid solution are then introduced into the reaction vessels by cannulas which pierce the septums and extend into the septum tube passages. After the reactant chemicals are introduced into the reaction vessels, the double action air cylinder 217 are actuated to close the plug valve 193 controlling the cannula tubes 191. Pressurized gas phase reactant is then introduced under high pressure into the reaction vessels, that is pressure up to at least as high as 200 psi.

During the low and high pressurization of the reaction vessels as well as during the introduction of the reaction chemicals, heat and/or cooling may be applied to the reaction vessels by means of the heat exchangers 49. The oppositely located heat exchangers 49 may be arranged so that one is supplying heat and the other supplying cooling so that a heat differential is obtained across the reaction vessels. Stirring of the contents of the reaction vessels also takes place during these time periods using rare earth magnetic stir bars 73 driven by stirring motors 71. Upon completion of the reactions, the reaction vessels are cooled, the gas is vented, diluents may be added with heating and stirring, if necessary, and the reaction contents transferred from the reaction vessels either by air transfer or by removing the cups 79 from their caps 81.

This invention includes a unique method of determining when the viscosity of the reacting solution reaches a desired value, in other words when the reaction is complete, using a single sensor 245 such as a Hall effect sensor, a magnetostrictive detector or even a loop of wire. This method is performed by turning on the stirring motor 241 at the beginning of the chemical reaction in the reaction vessel. The sensor 245 is used to measure the frequency of rotation of the magnetic stir bar 73, commencing at the beginning of the reaction and continuing during the reaction. When the stir bar decouples from the field of the stirring motor due to the increase in viscosity of reacting solution which results from the completion of the reaction, the sensor will measure either no signal or a value that is not compatible with the elapsed time of operation as set forth in the calibration table. This determination of the lapsed time for the stirring bar to decouple as shown on a calibration table will indicate the viscosity of the reacting chemicals when the reaction was completed.

I claim:

1. A reaction block assembly of reaction vessels for conducting chemical reactions under pressure, including:
   a heat conductive reaction block having at least one exterior side wall and at least one reaction vessel receiving opening formed in said block inwardly of said exterior side wall,
   a heat exchanger mounted in heat transfer engagement with said exterior side wall of said reaction block,
   a reaction vessel positioned in said reaction vessel receiving opening,
   a cap attached to said reaction vessel,
   a cannula opening formed in said cap,
   a cannula passage connected at one end to said cannula opening and having a septum at another end,
   a valve controlling said cannula passage, and
   an operating mechanism for opening and closing said cannula passage controlling valve.

2. The reaction block assembly of claim 1 in which said cannula passage controlling valve is a plug valve and said operating mechanism for opening and closing said cannula passage controlling valve includes a lever connected to said plug valve and an air cylinder connected to said lever.

3. The reaction block assembly of claim 1 in which a magnetic stir bar is located in said reaction vessel and a motor driven magnet is located adjacent said reaction block in driving alignment with said stir bar in said reaction vessel.

4. The reaction block assembly of claim 1 in which said heat conductive reaction block has at least two exterior side walls and at least a plurality of reaction vessel receiving openings formed in said block between said exterior side walls, a separate heat exchanger mounted in heat transfer engagement with each of said exterior side walls of said reaction block, a reaction vessel positioned in each of said plurality of reaction block vessel receiving openings, a cap attached to each of said reaction vessels, a cannula opening formed in each of said caps, a cannula passage connected at one end to each of said cannula openings and having a septum at another end, a valve controlling each of said cannula passages, an operating mechanism for opening and closing each of said cannula passage control valves, and each of said heat exchangers adapted to operate in a heat exchange mode different from the heat exchange mode of said other said heat exchanger to provide a temperature differential across said reaction block and said plurality of reaction vessels.

5. The reaction block assembly of claim 4 in which each of said cannula passage controlling valves is a plug valve and said operating mechanism for opening and closing said cannula passage controlling valves each includes a lever connected to each of said plug valves and an air cylinder connected to each of said cams.

6. The reaction block assembly of claim 4 in which a magnetic stir bar is located in each of said reaction vessels and a motor driven magnet is located adjacent said reaction block in driving alignment with each of said stir bars in each of said reaction vessels.

7. A reaction block assembly for pressurized chemical reactions in a reaction vessel, including:

a heat conductive reaction block having at least one reaction vessel receiving opening formed therein, a reaction vessel positioned in said reaction vessel receiving opening, said reaction vessel having an open end surrounded by a flange, a capture plate supported on said reaction block, an opening formed in said capture plate to receive said reaction vessel when said reaction vessel is positioned in said reaction vessel receiving opening of said reaction block, a cap closing said reaction vessel, said cap having an outwardly projecting ledge, an upper plate supported on said capture plate, an opening formed in said upper plate to receive said cap and a shoulder formed in said upper plate to capture said cap ledge, an aligned pair of grooves formed in said upper plate and extending radially outwardly from said opening in said upper plate, and radially extending pins projecting from said shoulder and adapted to be received in said grooves to orient said cap rotationally relative to said reaction block assembly.

8. The reaction block assembly of claim 7 in which a cannula passage opening is formed in a top of said cap, said cannula passage opening is located eccentrically relative to said reaction vessel receiving opening, and said grooves and said pins which orient said cap rotationally relative to said reaction block assembly do so by orienting said cannula passage opening relative to said reaction block assembly.

9. The reaction block assembly of claim 7 in which said heat conductive reaction block has a plurality of reaction vessel receiving openings formed therein, a reaction vessel is positioned in each of said reaction vessel receiving openings, each of said reaction vessels has an open end surrounded by a flange, a plurality of openings are formed in said capture plate to receive each of said reaction vessels when each of said reaction vessels is positioned in a reaction vessel receiving opening of said reaction block, a cap closing each reaction vessel, each of said caps having an outwardly projecting ledge, an opening formed in said upper plate to receive each of said caps and a shoulder formed in said upper plate to capture each of said cap ledges, an aligned pair of grooves formed in said upper plate adjacent each opening and extending radially outwardly from each of said openings, and radially extending pins projecting from each of said shoulders and adapted to be received in said grooves to orient said caps rotationally relative to said reaction block assembly.

10. The reaction block assembly of claim 9 in which a cannula passage opening is formed in the top of each cap, each of said cannula passages opening is located eccentrically relative to its reaction vessel receiving opening, and said groove and said pins which orient each of said cap rotationally relative to said rotational block assembly do so by orienting each of said cannula passages openings relative to said reaction block assembly.

* * * * *